United States Patent [19]

Winterfeldt et al.

[11] Patent Number: 5,430,202

[45] Date of Patent: Jul. 4, 1995

[54] PROCESS FOR THE PREPARATION OF SUBSTANTIALLY FLUORINATED ALKYL BROMIDES

[75] Inventors: Andreas Winterfeldt, Barsinghausen; Günter Bartels, Grossburgwedel; Reinhard Knieps, Hanover, all of Germany

[73] Assignee: Riedel-De Haen Aktiengesellschaft, Seelze, Germany

[21] Appl. No.: 293,564

[22] Filed: Aug. 22, 1994

Related U.S. Application Data

[63] Continuation of Ser. No. 975,581, Jan. 25, 1993, abandoned.

[30] Foreign Application Priority Data

Aug. 9, 1990 [DE] Germany .................. 40 25 227.2

[51] Int. Cl.$^6$ .................. C07C 17/20; C07C 19/08
[52] U.S. Cl. .................................................. 570/170
[58] Field of Search ...................... 570/170, 261

[56] References Cited

U.S. PATENT DOCUMENTS

| | | |
|---|---|---|
| 4,912,269 | 3/1990 | Drivon et al. . |
| 5,051,535 | 9/1991 | Werner .................. 570/170 |
| 5,336,818 | 8/1994 | Winterfeldt et al. .......... 570/170 |

OTHER PUBLICATIONS

Journal of the Chemical Society, Section "B", Physical Organic Chemistry, Part II, pp. 1347–2474 (1971).
Tetrahedron Letters, The International Organ for the rapid publication of preliminary communications in organic chemistry. Subject/Author Index numbers 1-5-2-1975 (1975).
"Methoden Der Organischen Chemie", A. Roedig: Herstellung von Bromverbindugen, pp. 354–360.

*Primary Examiner*—Alan Siegel
*Attorney, Agent, or Firm*—Connolly & Hutz

[57] ABSTRACT

According to the process according to the invention, substantially fluorinated alkyl bromides, preferably perfluoroalkyl bromides, are prepared by reaction of substantially fluorinated alkyl iodides, with phase transfer catalysts in the bromide form.

17 Claims, No Drawings

PROCESS FOR THE PREPARATION OF SUBSTANTIALLY FLUORINATED ALKYL BROMIDES

This application is a continuation, of application Ser. No. 07/975,581 filed Jan. 25, 1993 now abandoned.

The present invention relates to a process for the preparation of substantially fluorinated alkyl bromides, in particular of perfluoroalkyl bromides, starting from substantially fluorinated alkyl iodides, in particular from perfluoroalkyl iodides.

Substantially fluorinated alkyl bromides, in particular perfluoroalkyl bromides are used, for example, as intermediates for the preparation of polymer liquids, resins and elastomers, as X-ray contrast medium, for the preparation of pharmaceutical preparations and in aqueous emulsion as a blood substitute. A perfluoroalkyl bromide which is preferred as blood substitute is perfluorooctyl bromide.

A series of processes are already known for the preparation of perfluoroalkyl bromides. Thus, for example, according to Japanese Patent JP 601 84 033 (C.A. Vol. 104 (1986), 88106p) perfluoroalkyl iodides are reacted in the presence of free radical initiators with elemental bromine to give perfluoroalkyl bromides. Hazeldine (J. Chem. Soc. 1953, 3761-3768) describes on page 3763 and 3766 the reaction of perfluoroalkyl iodides with elemental bromine and with irradiation using UV light. Both methods have considerable problems associated with them in terms of materials and safety precautions, due to the use of elemental bromine, the release of elemental iodine, interhalogen compounds and hydrogen fluoride.

Examples of further preparation processes for perfluoroalkyl bromides are ($R_F$=perfluoroalkyl): reaction of bromine with compounds $R_F$—$SF_5$ at 500° C. in the presence of nickel (U.S. Pat. No. 3,456,024); reaction of bromine with compounds $R_F$—$SO_2Na$ in the presence of $KI/I_2$ (C.A., Vol. 107 (1987), 236043); reaction of bromine with salts of perfluorinated carboxylic acids (U.S. Pat. No. 2,678,953), in particular with $R_FCOOAg$ (U.S. Pat. No. 2,678,953) and Hauptschein et.al., J. Am. Chem. Soc. 74 (1952), 1347ff); reaction of bromine with compounds $R_FH$ with simultaneous irradiation using UV light (J. Chem. Soc. 1953, 3761). In all these processes, the use of elemental bromine leads to significant problems in terms of materials and safety precautions. Moreover, the starting compounds are difficult to obtain or have to be prepared from the corresponding perfluoroalkyl iodides via an additional process step. This is also true of the preparation of perfluoroalkyl bromides by reaction of $R_FSO_3Cl$ with HBr gas in the presence of a catalyst at 125° C. (EP-A1-0,298,870).

According to Fainberg et.al. JACS 79. 4172 (1957), perfluoroallyl bromide can be prepared by reaction of perfluoroallyl iodide with lithium bromide in acetone. Applying this transhalogenation to other perfluoroalkyl iodides is obvious but unsuccessful, since in normal perfluoroalkyl iodides there is no activation of iodine by an allyl group. As can be seen from Comparative Example 1 which follows, the reaction conditions described by Fainberg et. al. cannot be applied successfully to perfluorooctyl iodide. Comparative Examples 2 and 3 which follow show that the attempt of accelerating the reaction by phase transfer catalysis does not lead to a satisfactory result either.

The result of the comparative examples is as expected, since it is known that fluorine atoms considerably reduce the reactivity of alkyl halides in nucleophilic substitution reactions (cf., for example, Houben-Weyl, Methoden der organischen Chemie (Methods of Organic Chemistry), 4th Edition, Vol. 5/4, p. 685, 688).

The previously known processes for preparing substantially fluorinated alkyl bromides, in particular perfluoroalkyl bromides, are not satisfactory for the above-mentioned reasons. Accordingly, the object of the present invention is to provide a technically simple process for preparing substantially fluorinated alkyl bromides, in particular perfluoroalkyl bromides, starting from the easily accessible substantially fluorinated alkyl iodides, in particular perfluoroalkyl iodides.

Surprisingly, it has been found that when equimolar amounts of a phase transfer catalyst present in the bromide form are used, substantially fluorinated alkyl bromides, preferably perfluoroalkyl bromides, are accessible in a single reaction from the corresponding substantially fluorinated alkyl iodides, preferably perfluoroalkyl iodides.

The invention relates to a process for the preparation of substantially fluorinated alkyl bromides, starting from substantially fluorinated alkyl iodides. The process according to the invention is characterised in that the substantially fluorinated alkyl iodide is reacted with a phase transfer catalyst present in the bromide form in a molar ratio of 1:(0.4 to 3).

The term "substantially fluorinated" means that in the alkyl bromides or alkyl iodides predominantly fluorine atoms and only one or a few hydrogen atoms, preferably no hydrogen atom, are present apart from the bromine atom or iodine atom. The process according to the invention is suitable in particular for preparing substantially fluorinated alkyl bromides of the formula I $$X—C_nF_{2n}—Br \qquad (I)$$

in which X is H, F or $(F_3C)_2CF$— and n is 1 to 20, preferably 4 to 16 and particularly preferably 6 to 12. In formula I, the group —$C_nF_{2n}$— has in particular the form $$—(CF_2)_n— \qquad (II).$$

To prepare a substantially fluorinated alkyl bromide by the process according to the invention, a substantially fluorinated alkyl iodide is used. This is understood to mean a compound which differs from the desired final product only by the exchange of iodine for bromine. Accordingly, in the process according to the invention, the starting materials preferably used are compounds of the formula III $$X—C_nF_{2n}—I \qquad (III)$$

in which X, n and $C_nF_{2n}$ have the already mentioned meaning.

In formulae I and III, X is preferably $(F_3C)_2$—CF— and particularly preferably F. Accordingly, the process according to the invention is suitable in particular for preparing perfluoroalkyl bromides, particularly preferably those having 6 to 12 C atoms, very particularly preferably for preparing perfluorooctyl bromide.

The substantially fluorinated alkyl iodides used as starting materials, in particular the compounds of the formula III, are known and/or can be prepared by various processes known for this class of compounds.

Any organic compound in which bromine is present in anionic form and which has sufficient solubility in the reaction medium can be used as phase transfer catalyst. Suitable phase transfer catalysts are in particular bromides of quaternary organic compounds, such as, for example, quaternary ammonium, phosphonium and arsonium compounds of the general formulae IV, V and VI:

  (IV)

  (V)

  (VI)

In phase transfer catalysts of this type, the four radicals R can be identical or different and/or also have functional groups. The radicals R can be, for example, alkyl radicals having 1 to 20 C atoms, phenyl or benzyl radicals. Suitable central onium atoms are, apart from nitrogen, phosphorus and arsenic, also other atoms, such as, for example, antimony or sulphur. Examples of suitable phase transfer catalysts are: $(CH_3)_4NBr$; $(C_2H_5)_4NBr$; $(C_3H_7)_4NBr$; $(C_4H_9)_4NBr$; $(C_8H_{17})_3NCH_3Br$; $C_6H_5CH_2N(C_2H_5)_2Br$; $C_6H_{13}N(C_2H_5)_3Br$; $C_8H_{17}N(C_2H_5)_3Br$; $C_{10}H_{21}N(C_2H_5)_3Br$; $C_{12}H_{25}N(C_2H_5)_3Br$; $C_{16}H_{33}N(CH_3)_3Br$; $C_{16}H_{33}N(C_2H_5)_3Br$; $(C_6H_5)_4PBr$; $(C_6H_5)_3PCH_3Br$; $(C_8H_{17})_3PC_2H_5Br$; $C_{16}H_{33}P(C_2H_5)_3Br$.

Quaternary ammonium or phosphonium bromide are preferably used. Quaternary phosphonium bromides, in particular tetraalkylphosphonium bromides, having 1 to 20 C atoms in the individual alkyl radicals, such as, for example, tetrabutylphosphonium bromide is particularly preferred. A mixture of various phase transfer catalysts can also be used.

The preparation of the phase transfer catalysts mentioned is known. Many are commercially available.

The reaction according to the invention is carried out by simply mixing the substantially fluorinated alkyl iodide with the phase transfer catalyst. The addition of a solvent is not required. However, the reaction can also be carried out in a suitable solvent or solvent mixture.

The amount of phase transfer catalyst used per mole of substantially fluorinated alkyl iodide is such that sufficient conversion is obtained. Preferably, 0.4 to 3 mol, preferably 0.5 to 2 mol, and very particularly preferably 0.8 to 1.4 mol, of phase transfer catalyst in the bromide form are used per mole of substantially fluorinated alkyl iodide. In many cases, the molar ratio of substantially fluorinated alkyl iodide to phase transfer catalyst is 1:1 to about 1:1.

It is also possible to use more than 3 mol of phase transfer catalyst per mole of substantially fluorinated alkyl iodide. However, this does not bring any advantages. If the amounts of phase transfer catalyst are too small, only insufficient conversion is obtained.

The phase transfer catalyst can be used as solid or also in the form of an aqueous solution. If it is used as an aqueous solution, the water is distilled off from the reaction mixture before the actual reaction. This removal of water by distillation is advantageously carried out azeotropically with recycling of the organic phase into the reaction mixture.

The reaction temperature is preferably between 0° C. and the boiling point of the reaction mixture under atmospheric pressure. The reaction is carried out in particular at a temperature of 20° C. to the boiling point of the reaction mixture under atmospheric pressure, preferably up to the boiling point of the substantially fluorinated alkyl iodide under atmospheric pressure. In many cases, the reaction is carried out at temperatures of 50° to 140° C. The reaction rate is, as is usual, greater at higher temperatures than at lower temperatures.

It may be advantageous to carry out the reaction under an inert gas atmosphere, for example under argon.

The reaction and work-up can take place in different ways and, for example, be carried out such that substantially fluorinated alkyl bromide formed is distilled off during the reaction or after the reaction. The work-up can also preferably be carried out such that after the reaction, the temperature of the reaction mixture is, if desired, lowered and water is added to the reaction mixture, i.e. the reaction mixture is mixed, and the mixture is then separated into an aqueous and an organic phase and the separated organic phase is separated into its components by distillation, i.e. in particular into substantially fluorinated alkyl bromide and unconverted substantially fluorinated alkyl iodide. The starting materials recovered in this work-up can again be added to the reaction.

The phase transfer catalyst present after the end of the reaction as an iodide/bromide mixture can be reconverted to the pure bromide by conventional methods. In the preferred work-up of the reaction mixture (addition of water to the reaction mixture, phase separation), the remaining aqueous phase contains the phase transfer catalyst as an iodide/bromide mixture.

In order to convert the iodide portion into the bromide form, the aqueous phase can be subjected to ion exchange, in which iodide is exchanged for bromide. Polymer ion exchanges suitable for this purpose are known. The aqueous solution of the phase transfer catalyst in the bromide form formed in the ion exchange can, as already mentioned, be used directly for the reaction according to the invention. However, it is also possible to isolate the phase transfer catalyst from the aqueous solution in solid form and then use it again for carrying out the reaction according to the invention.

In the process according to the invention, the desired substantially fluorinated alkyl bromides, preferably perfluoroalkyl bromides, are obtained in yields of up to more than 90% (relative to converted starting material). The unconverted starting materials can be recovered in a similar manner and used again. The phase transfer catalyst in the bromide form is used in the reaction according to the invention not as a catalyst but as a reaction component and a large portion of it is converted during the reaction to the corresponding iodide form. The iodide form can easily be reconverted into the bromide form and then used again. The purities of the final products determined by gas chromatography are high and in many cases above 99%.

The invention is further illustrated by means of the examples below:

EXAMPLE 1

968 g of perfluorooctyl iodide (1.81 mol) and 613 g of tetrabutylphosphonium bromide (1.81 mol) are refluxed for 8 hours.

At a maximum bottom temperature of 160° C., perfluorooctyl bromide is then slowly distilled off at a column head temperature of 140°-143° C. Distillation of the reaction mixture is then continued in vacuo (18 mbar).

After cooling to 90° C., 250 ml of water are added to the bottom product, and unconverted perfluorooctyl iodide is distilled off azeotropically. After phase separation, the distillates are combined, washed with sodium disulphite and then subjected to fractional distillation.

Yield: 540 g of perfluorooctyl bromide 340 g of perfluorooctyl iodide, i.e. 60% of theory of perfluorooctyl bromide or 91% of theory, relative to converted perfluorooctyl iodide. B.p.: 142°-143° C. GC: Purity greater than 99%

The remaining residue of 500 g is dissolved in a total of 4500 g of 20% strength methanol, stirred with 5 g of activated carbon, filtered and is suitable in this form for regeneration on polymer ion exchanger resins.

EXAMPLE 2

In a repetition of Example 1, tetrabutylphosphonium bromide is used in the form of an aqueous solution. Before the actual reaction, the water is distilled off azeotropically while recycling the organic phase. The reaction mixture is then heated at 140° C. for 18 hours, cooled to room temperature and mixed with 500 ml of water. The phases are separated, and the organic phase is washed with sodium disulphite and then subjected to fractional distillation.

Yield: 530 g of perfluorooctyl bromide 345 g of perfluorooctyl iodide, i.e. 58% of theory of perfluorooctyl bromide or 90% of theory relative to converted perfluorooctyl iodide B.p.: 142°-143° C. GC: Purity greater than 99%

The comparative example below shows that the reaction conditions given by Fainberg et al. JACS 79, 4172 (1957) for the preparation of perfluoroallyl bromide cannot be applied to the preparation of perfluorooctyl bromide. Comparative Examples 2 and 3 below show that even if the reaction is carried out under phase transfer conditions no useful yields of perfluorooctyl bromide are obtained.

COMPARATIVE EXAMPLE 1

100 g of perfluorooctyl iodide (183 mmol) are added to a solution of 19 g of LiBr (220 mmol) in 150 ml of dry acetone over a period of 10 minutes, and the mixture is then refluxed for 8 hours. It is poured into 500 ml of water, the organic phase is separated off and dried with a small amount of CaCl$_2$.

Yield: 100 g of perfluorooctyl iodide 95% pure. Perfluorooctyl bromide cannot be detected by gas chromatography.

COMPARATIVE EXAMPLE 2

100 g of perfluorooctyl iodide (183 mmol), 75 g of CaBr$_2$ (375 mmol), 25 ml of water and 1 g of tetrabutylammonium bromide (1.5 mol %) are refluxed for 5 hours. The mixture is poured into 500 ml of water, the organic phase is separated off, washed until free of halide and dried with a small amount of CaCl$_2$. Yield: 94 g GC: 1% of perfluorooctyl bromide 96 % of perfluorooctyl iodide

COMPARATIVE EXAMPLE 3

Analogously to Comparative Example 2, the following is obtained using 1 g of tetrabutylphosphonium bromide (1.5 mol %) as phase-transfer catalyst:

Yield: 95 g GC: 1% of perfluorooctyl bromide 97% of perfluorooctyl iodide

We claim:

1. Process for the preparation of substantially fluorinated alkyl bromides, starting from substantially fluorinated alkyl iodides, characterised in that a substantially fluorinated alkyl iodide is reacted with a phase transfer catalyst present in the bromide form wherein the amount of fluorinated alkyl iodide to the phase transfer catalyst is in a molar ratio of 1:(0.4 to 3).

2. Process according to claim 1, characterized in that for the preparation of substantially fluorinated alkyl bromides of the formula I

$$X-C_nF_{2n}-Br \qquad (I)$$

in which X is H, F or (F$_3$C)$_2$CF— and n is 1 to 20, a compound of the formula III

$$X-C_nF_{2n}-I \qquad (III)$$

is used as substantially fluorinated alkyl iodide.

3. Process according to claim 2, characterized in that in formulae I and III the group —C$_n$F$_{2n}$—has the form —(CF$_2$)$_n$— and/or X has the meaning (F$_3$C)$_2$CF—.

4. Process according to claim 1, characterized in that the phase transfer catalyst used in the bromide form is a quaternary ammonium bromide.

5. Process according to claim 1, characterised in that the phase transfer catalyst used in the bromide form is tetrabutylphosphonium bromide.

6. Process according to claim 1, characterized in that the substantially fluorinated alkyl iodide and the phase transfer catalyst in the bromide form are used in a molar ratio of 1:(0.5 to 2).

7. Process according to claim 1, characterized in that the reaction is carried out at a temperature of 20° C. up to the boiling point of the reaction mixture.

8. Process according to claim 1, characterised in that after the reaction is complete the reaction mixture is mixed with water and the mixture is then separated into an aqueous and an organic phase and the organic phase is then separated into its components by distillation.

9. Process according to claim 1, characterised in that substantially fluorinated alkyl iodide recovered during work-up is again used as starting material and/or the iodide/bromide mixture of the phase transfer catalyst formed during work-up is reconverted into the bromide form and used again.

10. Process according to claim 1, characterised in that perfluorooctyl iodide is used as substantially fluorinated alkyl iodide.

11. The process according to claim 2, wherein n is 4 to 16.

12. The process according to claim 2, wherein n is 6 to 12.

13. The process according to claim 2, wherein X is F.

14. The process according to claim 1, wherein the phase transfer catalyst is quaternary phosphonium bromide.

15. The process according to claim 6, wherein the molar ratio is 1:(0.8 to 1.4).

16. The process according to claim 6, wherein the molar ratio is about 1:1.

17. The process according to claim 7, wherein reaction is carried out at a temperature of 50° to 140° C.

* * * * *